(12) United States Patent
Gaudio

(10) Patent No.: US 9,299,143 B2
(45) Date of Patent: Mar. 29, 2016

(54) METHODS FOR IMAGE PROCESSING

(71) Applicant: VARIAN MEDICAL SYSTEMS, INC., Palo Alto, CA (US)

(72) Inventor: Stephen Gaudio, Mountain View, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 0 days.

(21) Appl. No.: 14/858,330

(22) Filed: Sep. 18, 2015

(65) Prior Publication Data

US 2016/0012584 A1    Jan. 14, 2016

Related U.S. Application Data

(63) Continuation of application No. 14/040,591, filed on Sep. 27, 2013, now Pat. No. 9,142,016.

(51) Int. Cl.
| | |
|---|---|
| *G06K 9/00* | (2006.01) |
| *G06T 7/00* | (2006.01) |
| *A61N 5/10* | (2006.01) |
| *G21K 5/00* | (2006.01) |

(52) U.S. Cl.
CPC ............ *G06T 7/0012* (2013.01); *A61N 5/1075* (2013.01); *G06T 2207/10116* (2013.01)

(58) Field of Classification Search
USPC ......... 382/100, 103, 106–107, 128–134, 162, 382/268, 173, 181, 199, 201, 219, 232, 254, 382/274, 276, 286–294, 305, 312; 378/2, 378/20, 21, 65, 207, 64, 196
See application file for complete search history.

(56) References Cited

U.S. PATENT DOCUMENTS

| | | | | |
|---|---|---|---|---|
| 7,471,765 B2 * | 12/2008 | Jaffray | ................... | A61B 6/032 378/196 |
| 2008/0101669 A1 * | 5/2008 | Jeung | ....................... | A61B 6/08 382/128 |
| 2010/0303210 A1 * | 12/2010 | Beaumont | ............ | A61N 5/1048 378/207 |
| 2011/0228906 A1 * | 9/2011 | Jaffray | ................... | A61B 6/032 378/65 |
| 2013/0121457 A1 * | 5/2013 | Maltz | ..................... | A61B 6/032 378/4 |

OTHER PUBLICATIONS

Notice of Allowance for U.S. Appl. No. 14/040,591 dated May 20, 2015 (11 pages).

* cited by examiner

*Primary Examiner* — Seyed Azarian
(74) *Attorney, Agent, or Firm* — Vista IP Law Group, LLP

(57) ABSTRACT

An image processing method includes: obtaining an image that includes a ball image and a cone image; obtaining an estimate of a center of the ball image; converting the image to a converted image using a processor based at least in part on the estimate of the center of the ball image, wherein the converted image comprises a converted ball image that looks different from the ball image in the image, and a converted cone image that looks different from the cone image in the image; identifying the converted ball image in the converted image; and analyzing the converted ball image to determine a score that represents an accuracy of the estimate of the center of the ball image.

29 Claims, 14 Drawing Sheets

METHODS FOR IMAGE PROCESSING

RELATED APPLICATION DATA

This application is a continuation of U.S. patent application Ser. No. 14/040,591, filed on Sep. 27, 2013, pending, the entire disclosure of which is expressly incorporated by reference herein.

FIELD

This application relates generally to methods for image processing and, more specifically, to methods for finding and testing the alignment of radiation isocenter and mechanical isocenter.

BACKGROUND

A radiation oncology treatment system must be properly calibrated to ensure that the radiation beams accurately target the treatment volume. Calibration of the radiation isocenter is one of the quality control procedures to determine the accuracy of the treatment system. In short, the radiation isocenter is the point in space where radiation beams intersect when the gantry rotates around the gantry rotation axis. More specifically, the point where the central radiation beams intersect is a small volume that looks geometrically similar to a sphere or an ellipsoid, and the center-of-mass of this volume is the radiation isocenter. The radiation isocenter differs from the mechanical isocenter; the radiation isocenter is the point in space through which the central beam of radiation passes, whereas mechanical isocenter is the point where the targeting optical beams intersect (or where the gantry rotation axis and the collimator rotation axis intersect). When properly calibrated, the targeting optical beams of the treatment system that are used to target the radiation beams at intended target should intersect at radiation isocenter, but the two isocenters do not necessarily coincide.

Traditionally, the radiation isocenter is found by exposing radiographic film with a star shot pattern. The film is placed so that the beam enters through the edge of the film when it is irradiated from several gantry angles with a small field. The rotation axis of the gantry, running perpendicularly through the film, is marked. The middle lines of the three radiation beams, shown as stripes on the film, form a triangle when they intersect in the film center. The smallest circle which fits inside the triangle (all three beams have to intersect the circle or at least touch it) is usually called the radiation isocenter circle. Its size (diameter or radius) can be used to determine a quality parameter of the linac.

An alternative to find the radiation isocenter is the Winston-Lutz test (WL test), which characterizes specific aspects of Clinac treatment beam dose distribution error based on treatment beam test images. The Winston-Lutz test is becoming more widely adopted as the test for geometric positioning accuracy of the Clinac for its simplicity and similarity to the actual treatment: the cone represents the beam-shaping elements (e.g., the collimator), and the ball represents the tumor, located nominally at isocenter. The WL test if performed by having a lead ball on a rod is held in place and aligning the center of the lead ball with the targeting optical beams. The lead ball is then exposed to film or digital imager in different combinations of the gantry angles and the table angles. The isocenter is then calculated by locating the center point of the image of the ball, which is done by using conventional method of finding the mid point of the ball image via a ruler.

The Winston-Lutz test has many drawbacks, however. The beam scattering and penumbra effects will cause an unavoidable blurring of the image edge thus resulting in uncertainty of the true edge of the ball image and the calculated eccentricity. The resolution of the film and digital imager must also be high (~0.1 mm) in order to accurately find the edge of the ball image under magnification. In addition, visually estimating the image edge is susceptible to random noise present in the image, especially in conventional films.

SUMMARY

An image processing method includes: obtaining an image that includes a ball image and a cone image; obtaining an estimate of a center of the ball image; converting the image to a converted image using a processor based at least in part on the estimate of the center of the ball image, wherein the converted image comprises a converted ball image that looks different from the ball image in the image, and a converted cone image that looks different from the cone image in the image; identifying the converted ball image in the converted image; and analyzing the converted ball image to determine a score that represents an accuracy of the estimate of the center of the ball image.

Optionally, the image is converted to the converted image using a polar-to-rectangular coordinate conversion scheme.

Optionally, the converted ball image has a non-circular shape.

Optionally, the act of identifying the converted ball image is performed by the processor, which analyzes the converted image to identify a region in which the converted ball image lies.

Optionally, the act of analyzing the converted ball image comprises: calculating standard deviation values for a plurality of respective rows of pixels that correspond to the converted ball image; and summing the standard deviation values to obtain the score.

Optionally, the obtained image also includes a rod image, and the method further comprises identifying the rod image in the obtained image.

Optionally, the rod image in the image is excluded before converting the image to the converted image.

Optionally, the method further includes determining a center of the ball image based at least in part on the score.

Optionally, the obtained image also includes a rod image, and the method further comprises using the processor to determine a position of the rod image using an algorithm.

Optionally, the method further includes determining an additional center of the ball image based at least in part on the determined position of the rod, the additional center of the ball image being more accurate than the previously determined center of the ball image.

Optionally, the method further includes determining one or more additional scores for one or more additional estimates of the center of the cone image, wherein the center of the ball image is determined by selecting one of the estimates that has the lowest score.

Optionally, the method further includes using the processor to determine a center of the cone image.

Optionally, the method further includes determining an eccentricity between the determined center of the ball image and the determined center of the cone image.

Optionally, the eccentricity comprises an offset distance between the determined center of the ball image and the determined center of the cone image, and a direction of the offset distance.

Optionally, the offset distance is expressed in pixel values, and the method further comprises converting the offset distance from pixel values to length units.

Optionally, the method further comprises using the determined center of the ball image and one or more other parameters to determine one or more of an isocenter sag, isocenter skew, quality data representing measurement quality, and panel shift.

A computer product includes a non-transitory medium storing a set of instructions, an execution of which will cause an imaging method to be performed, the method comprising: obtaining an image that includes a ball image and a cone image; obtaining an estimate of a center of the ball image; converting the image to a converted image based at least in part on the estimate of the center of the ball image, wherein the converted image comprises a converted ball image that looks different from the ball image in the image, and a converted cone image that looks different from the cone image in the image; identifying the converted ball image in the converted image; and analyzing the converted ball image to determine a score that represents an accuracy of the estimate of the center of the ball image.

An image processing method includes: obtaining an image that includes a ball image and a cone image; using a processor to execute a first algorithm to determine a ball center; using the processor to execute a second algorithm to determine a cone center; and determining an eccentricity between the determined ball center and the determined cone center; wherein the first algorithm involves converting the ball image to a converted ball image that looks different from the ball image.

Optionally, the eccentricity comprises an offset distance between the determined ball center and the determined cone center, and a direction of the offset distance.

Optionally, the offset distance is expressed in pixel values, and the method further comprises converting the offset distance from pixel values to length units.

Optionally, the converted ball image has a non-circular shape.

Optionally, the second algorithm involves converting the cone image to a converted cone image that looks different from the cone image.

Optionally, the method further includes using the determined ball center and one or more other parameters to determine one or more of an isocenter sag, isocenter skew, quality data representing measurement quality, and panel shift.

A computer product includes a non-transitory medium storing a set of instructions, an execution of which will cause an imaging method to be performed, the method comprising: obtaining an image that includes a ball image and a cone image; executing a first algorithm by a processor to determine a ball center; executing a second algorithm by the processor to determine a cone center; and determining an eccentricity between the determined ball center and the determined cone center; wherein the first algorithm involves converting the ball image to a converted ball image that looks different from the ball image.

Other and further aspects and features will be evident from reading the following detailed description of the embodiments,

BRIEF DESCRIPTION OF THE DRAWINGS

The drawings illustrate the design and utility of various embodiments of the present application, in which similar elements are referred to by common reference numerals. In order to better appreciate how advantages and objects of the present application are obtained, a more particular description will be rendered by reference to specific embodiments thereof, which are illustrated in the accompanying drawings. Understanding that these drawings depict only typical embodiments and are not therefore to be considered limiting of its scope. The present application will be described and explained with additional specificity and detail through the use of the accompanying drawings in which.

DETAILED DESCRIPTION

Figure 1A:
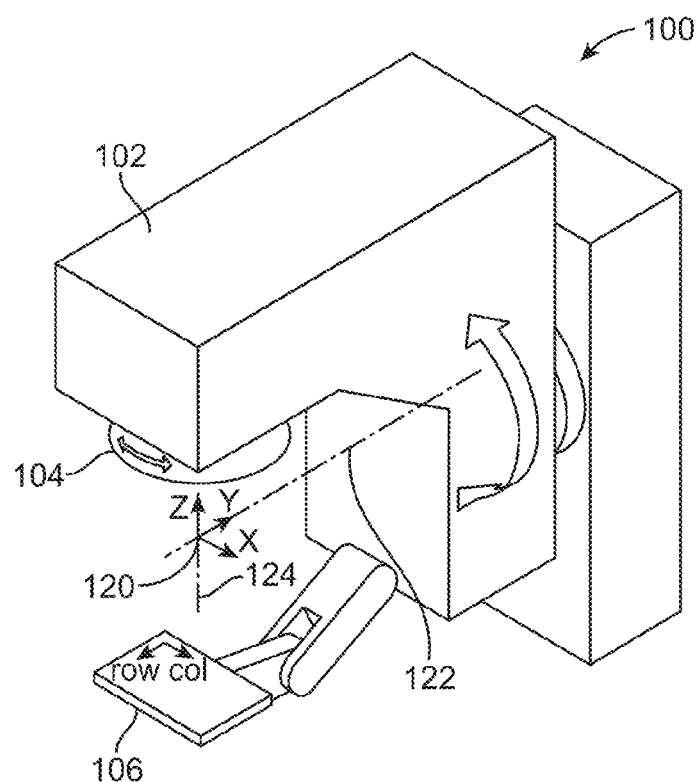
FIG. 1A illustrates a radiation system in accordance with some embodiments; illustrates a typical Winston-Lutz Test image acquired by a digital imager.

Various embodiments of the present application are described hereinafter with reference to the figures. It should be noted that the figures are not drawn to scale and elements of similar structures or functions are represented by like reference numerals throughout the figures. It should also be noted that the figures are only intended to facilitate the description of specific embodiments. They are not intended as an exhaustive description of the present application or as a limitation on the scope of the present application. In addition, an aspect or a feature described in conjunction with a particular embodiment is not necessarily limited to that embodiment and can be practiced in any other embodiments of the present application.

In the use of medical linear accelerators (or Clinac), the geometric positioning accuracy is an important quality control to radiation dose delivery. An exemplary medical linear accelerator is shown in FIG. 1A. The medical linear accelerator 100 includes a gantry 102, a collimator 104, and an imager 106. The mechanical isocenter 120 is the point of intersection of the gantry rotation axis 122 (e.g., Y-axis) and the collimator rotation axis 124 (e.g., Z-axis). The X-axis is defined as the axis extending from the intersection of the Y-axis and the Z-axis. The same accelerator 100 is shown in side view in FIG. 1B.

Figure 1B:
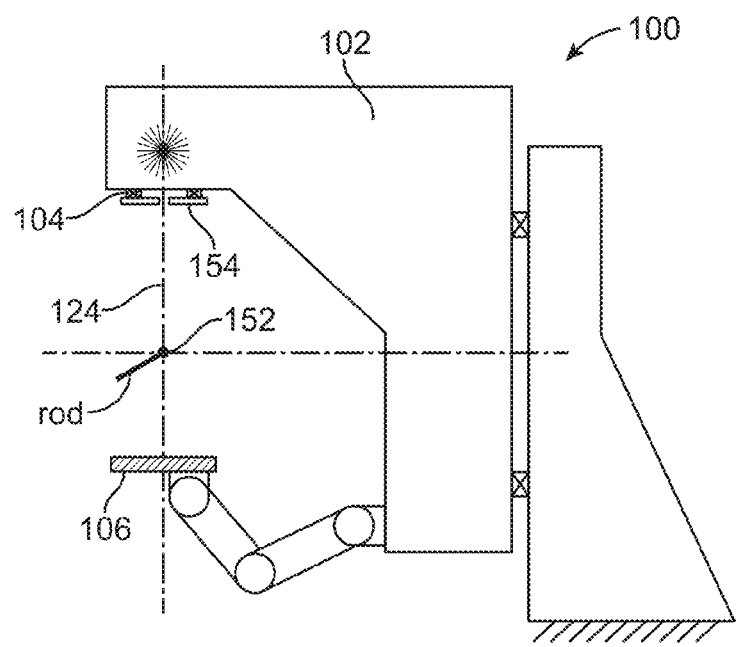
FIG. 1B illustrates the radiation system of FIG. 1A, particularly showing a Winston-Lutz Test being performed using a lead ball and cone.
Figure 3:
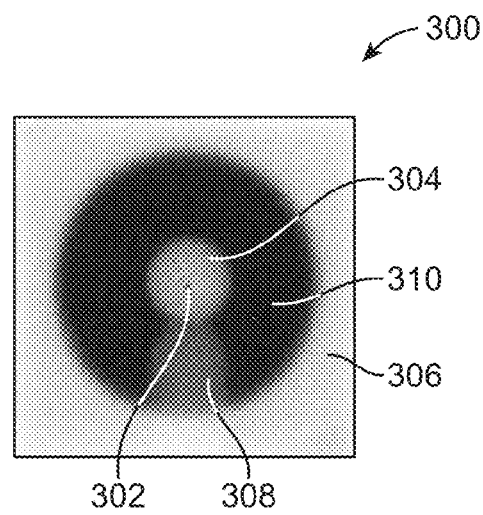
FIG. 3 illustrates an example of a digitized image of a Winston-Lutz Test.

One of the tests for geometric positioning accuracy of the medical linear accelerators is Winston-Lutz Test (an exemplary accelerator configured for Winston-Lutz Test is shown in FIG. 1B), which is performed by: (1) placing a lead ball (152 in FIG. 1B) where the center of the lead ball is aligned with the targeting optical beams (e.g., mechanically aligned with mechanical isocenter); (2) placing a lead cone 154 (FIG. 1B) is on the collimator so that cone center hole is aligned with the collimator rotation axis 124 (Z-axis); (3) acquiring images in different combinations of the gantry angles and collimator positions (e.g., an image is acquired for each arbitrary collimator position (i.e., the collimator rotational positions, which is the angular positions of the collimator achieved by rotating the collimator about axis 124) at each gantry angle, resulting in a set of N×M images, where N is the number of unique gantry positions, and M is the number of collimator positions); and (4) measuring isocenter manually based on the acquired images. The cone 154 has a circular opening for allowing radiation to go therethrough while the rest of the cone material blocks radiation. An example of a Winston-Lutz Test image is shown in FIG. 3. In an exemplary embodiment, an image is taken at each of the four different collimator positions at each of the four different gantry positions, 0°, 90°, 180°, and 270°, such that a total of 16 images are taken. The center point of the ball in each image is then determined.

An embodiment of the current image processing algorithm automates the determination of the precise location of the ball center and cone center in pixel coordinates based on the digital image acquired during Winston-Lutz test. The current method is objectively precise, immune to short scale noise and penumbra, checks for malfunction or calibration drift (long scale noise), automated, and faster determination of geometric position accuracy when compared to the conventional method of using visual estimation and ruler to measure the isocenter. In some cases, the precision may be at least $\frac{1}{100}^{th}$ of a pixel. The method also provides compensation factors to correct image shift error due to X-ray source deviations and imager panel mechanical shift, which may include gravity, positioning error, gantry bearing error, or similar disturbances.

Figure 2:
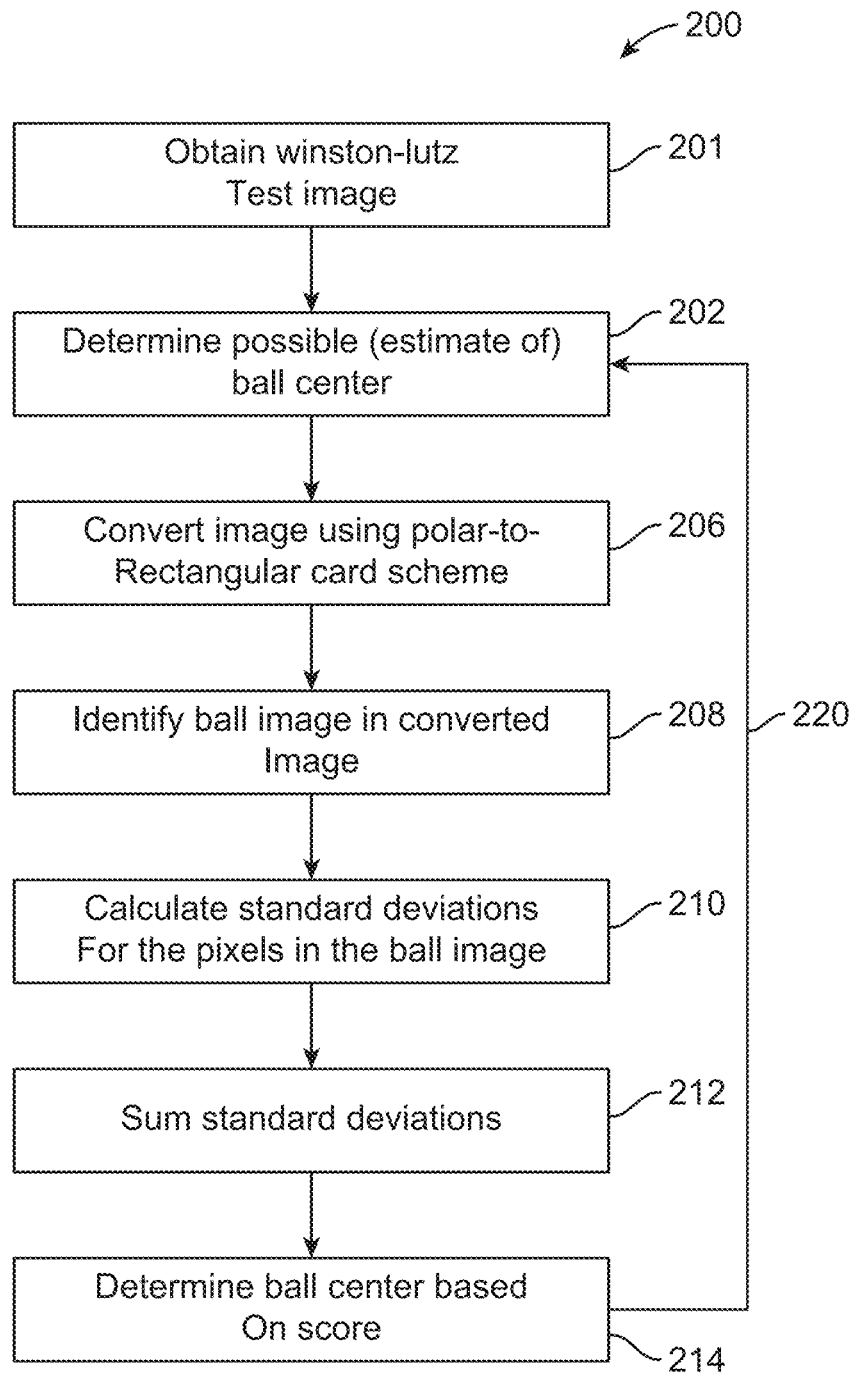
FIG. 2 illustrates a method for determining a center of a ball involved in a Winston-Lutz Test.

Referring now to the drawings, in which similar corresponding parts are identified with the same reference numeral. FIG. 2 is a method 200 for determining a center of the ball 152 in an image in accordance with some embodiments. The method 200 may be performed by a processor, which may be a part of the radiation system of FIG. 1A, or may be a part of another device that is configured to perform the features described herein. By means of non-limiting examples, the device that includes the processor configured to perform the features described herein may be a computer, an iPad, a Tablet, a smart phone, a handheld communication device, or any of other devices. The processor may be one or more of an ASIC processor, a FPGA processor, a signal processor, a general purpose processor, etc.

Referring now to FIG. 2, first, an image of a Winston-Lutz test is obtained (Item 201). In some embodiments, after the ball 152 is mounted, and the cone 154 is secured, radiation is delivered to obtain an image of the ball 152 and the cone 154. The image is generated using the detector 106 in response to radiation received by the detector 106. In some embodiments, the image provided by the detector 106 is a digitized image. In other embodiments, the image may be a film image that is converted to a digitized image by scanning and digitization. An example of the digitized image 300 of Winston-Lutz test is shown in FIG. 3. As shown in the figure, the image 300 includes an image 304 of the ball 152, an image 306 of the cone 154 (i.e., showing the boundary of the circular opening provided by the cone 154), and an image 308 of the rod that is connected to the ball. The image 300 also includes an area 310 representing unobstructed radiation that reaches the detector 106. Since the radiation not blocked by the ball 152 and the cone 154 will reach the detector 106, the area 310 formed by such radiation will have a color or greyscale that is distinctly different from the ball image 304 and the cone image 306.

In some embodiments, the act of obtaining the Winston-Lutz test image is performed by a processor receiving the image data of the Winston-Lutz test. In other embodiments, the act of obtaining the Winston-Lutz test image may also include generating the Winston-Lutz test image.

Returning to FIG. 2, next, a possible ball center is determined (Item 202). In some embodiments, a user may manually select a point near the center pixel of the ball portion of the grayscale digitized ball on an image acquired during the Winston-Lutz test. An example of the digitized image 300 of Winston-Lutz test with a selected ball center 302 is shown in FIG. 3. The initial guess of the center of the ball may be input manually by the user as a coordinate (x, y). In some embodiments, the act of determining the possible center in item 202 may be performed by the processor receiving input from the user regarding the initial guess of the ball center. In other embodiments, the initial guess may be automatically determined by the processor, which analyzes the image to make an initial guess of the ball center.

Figure 4:
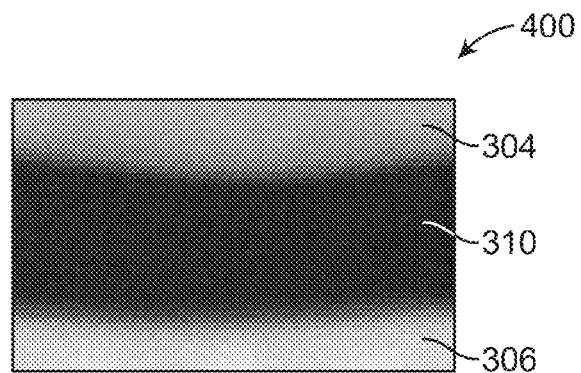
FIG. 4 illustrates an example of a converted image that has been converted using a polar-to-rectangular coordinate scheme.

Returning to FIG. 2, next, the image 300 is converted to a converted image using a polar to rectangular scheme, similar to a Mercator projection, based on the previously designated coordinate of the initially selected center (Item 206). An example of the converted image 400 that is converted from polar coordinate to rectangular coordinate based on the selected ball center is shown in FIG. 4. The converted image 400 includes an image 304 of the ball expressed in rectangular coordinate, and an image 306 of the cone also expressed in rectangular coordinate. The converted image 400 also includes the area 310 representing unobstructed radiation detected by the detector 106. In some embodiments, the act of converting the image 300 to the converted image 400 may be performed by the processor. Also, in some embodiments, the act of converting the image 300 to the converted image 400 may be performed automatically by the processor.

In some embodiments, the zone/image 308 of the rod may be omitted or discarded when converting the image 300 to the converted image 400. In one implementation, the position of the rod image 308 may be estimated and input manually to the processor. In other embodiments, the processor may automatically estimate the position of the rod image 308 by performing image analysis on the image 300/400. It is desirable to discard the rod image 308 from the converted image 400 because doing so will result in the ball image 304 being easier to be identified in the converted image 400. In some embodiments, the identification of the rod image 308 may be achieved by identifying a rod angle, which is the angle in the polar coordinate at which the rod image 308 lies. In other embodiments, the identification of the rod image 308 may be achieved by identifying a horizontal position in the converted image 400 at which the center of the rod image 308 lies.

Returning to FIG. 2, next, the image 304 of the ball 152 (converted ball image) is identified in the converted image 400 (Item 208). In some embodiment, because the area 310 has a color or darkness that is distinguishable from that of the image 304 of the ball 152, the image 304 of the ball 152 may be identified based on the difference in the color or darkness between the regions 304, 310. For example, the processor may select all of the pixels above the area 310 that have a color or darkness different (e.g., with the difference being above a certain prescribed threshold) from that in the area 310 as the image pixels for the ball 152. In some embodiments, the identification of the image 304 that corresponds with the ball 152 in the converted image 400 may be performed using the processor. Also, in some embodiments, the identification of the image 304 that corresponds with the ball 152 may be performed automatically by the processor.

Next, the standard deviations for the plurality of pixel rows of the zone 304 wherein the ball lies (the portion 304 in the converted image 400) is calculated (Item 210). In some embodiments, greyscale luminance values are used for calculating the standard deviations. In the illustrated embodiments, the standard deviations are calculated row-by-row, and so there are multiple standard deviation values for the respective rows. In some embodiments, the calculation of the standard deviation may be performed by the processor. Also, in some embodiments, the calculation of the standard deviation may be performed automatically by the processor.

Next, the row-wise standard deviation values are summed up to obtain an eccentricity score (Item 212). The eccentricity score represents how well the estimate (e.g., (x, y)) lies in the actual center of the ball image. In some embodiments, the eccentricity score may represent the eccentricity of the determined ball center (i.e., an amount of difference between the estimated ball center and the actual center of the ball 152), wherein a lower score represents less eccentricity, and therefore, a more accurate estimate. In other embodiments, the eccentricity score also represent the quality of the image data, which may indicate possible malfunction(s) in the Clinac operation. In some embodiments, item 212 may be performed by the processor. Also, in some embodiments, item 212 may be performed by the processor automatically.

Figure 5:
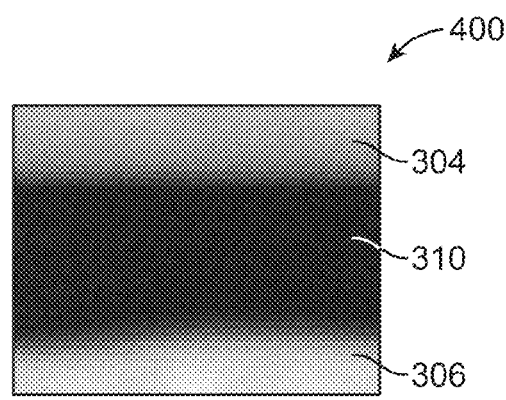
FIG. 5 illustrates another example of a converted image that has been converted using a polar-to-rectangular coordinate scheme.

Next, the center of the ball 152 is determined based at least in part on the eccentricity score (item 214). In some embodiments, the above algorithm may be repeated with one or more center estimate(s) to obtain one or more corresponding eccentricity score(s). In particular, item 202 may be repeated one or more times for one or more ball center estimate(s), and items 206-214 may be repeated one or more corresponding times to determine one or more eccentricity scores (see loop arrow 220). This may be performed until an estimated ball center with the best eccentricity score is obtained. The ball center estimate with the lowest corresponding eccentricity score is then selected as the center of the ball 152. In some embodiments, a determined eccentricity score may be used to determine a next estimate of the center of the ball 152. Also, in some embodiments, an optimization algorithm may be employed by the processor to minimize the eccentricity score, to thereby find the optimized/actual center of the ball 152 in the image. When the actual center of the ball is determined, or the eccentricity score is minimized, the converted image 400 converted from the image 300 based on the determined actual center will show the image 304 for the ball 152 having a relatively uniform shape (like that shown in FIG. 5). In some embodiments, item 214 may be performed by the processor. Also, in some embodiments, item 214 may be performed by the processor automatically.

In some embodiments, the determined center of the ball 152 from item 214 may be stored in a non-transitory medium for later use or processing.

Figure 6:
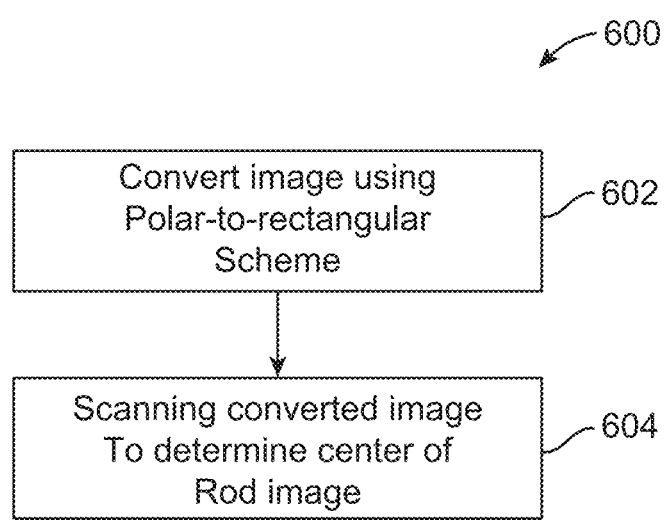
FIG. 6 illustrates a method for determining a rod position involved in a Winston-Lutz Test.
Figure 7:
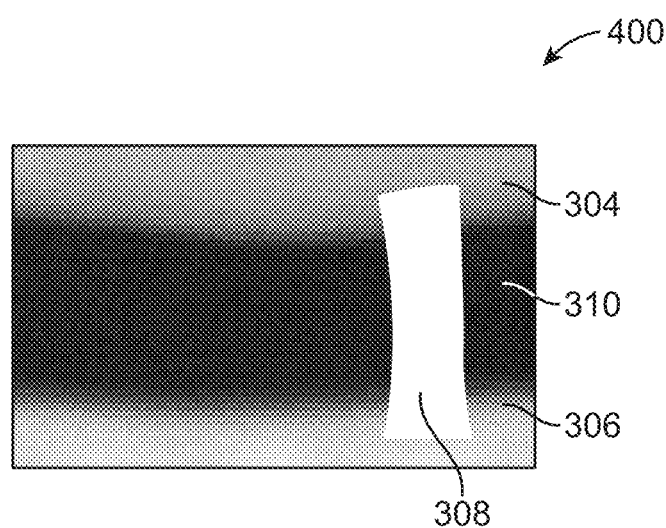
FIG. 7 illustrates an example of a converted image that includes a rod image.

As discussed, in some embodiments, the position of the rod image 308 may be initially estimated, so that it can be discarded in the converted image 400. In some embodiments, after the ball center is initially determined from item 214, the position of the rod image 308 may be verified and/or fine-tuned to potentially improve the accuracy of the ball center determination. FIG. 6 illustrates an image processing method 600 for determining a rod position. First, after the ball center has been determined from item 214, the image 300 is converted into a converted image 400 using a polar to rectangular scheme, similar to a Mercator projection, based on the coordinate of the determined ball center (Item 602). The act of item 602 may be similar to that of item 206. When the image 300 is converted into the converted image 400, the rod image 308 is retained so that the converted image 400 will include an image of the rod. An example of the converted image 400 with the rod image 308 is shown in FIG. 7.

Returning to FIG. 6, next, the approximate center of the rod image 308 may be determined by scanning horizontally the converted image 400 (Item 604). In some embodiments, the processor may look for a maximum brightness pixel for each horizontal row. The horizontal position in each row where the maximum brightness pixel is located represents the rod position (e.g., position of the centerline of the rod) at that row. In other embodiments, the position of the centerline of the rod in each row may be determined based on secondary order interpolation of the pixels adjacent to the maximum brightness pixel. In such technique, the brightest pixel is first found. Then that pixel and the two pixels on either side of the brightest pixel are used to feed a second order interpolator to calculate a theoretical center of the rod. This may be useful in case the center of the rod is straddling two pixels.

After the position of the centerline of the rod is determined for each row, the positions are averaged to determine the rod position. In some embodiments, the rod position (e.g., X=34 mm) in the rectangular coordinate format may be converted to polar coordinate format (e.g., R=24°).

In some embodiments, after the rod position has been objectively determined using the method 600 of FIG. 6, the method of FIG. 2 may be repeated using (1) the rod position determined from item 604, and (2) the position of the ball center determined previously from item 214, to obtain a more precise ball center. In particular, when repeating the method of FIG. 2, the rod position determined objectively from the method 600 of FIG. 6 may be used by the processor to omit the rod image zone when converting the image 300 to the converted image 400 (in item 208) based on the previously determined ball center. Because the rod position is objectively determined, it is subject to less variation that may otherwise result from manual interpretation. As a result, the rod image 308 that is selected for exclusion when converting the image 300 to the converted image 400 is more accurate. This result in a determination of the ball center (from item 214) that is more accurate.

In other embodiments, the method 600 for determining rod position objectively is optional, and may not be performed. In such cases, the method 200 may not be repeated. In particular, in other embodiments, the ball center position obtained from item 214 in the method 200 the first time around may be used as the final ball center position.

Also, in other embodiments, after the method 600 is performed to objectively determine the rod position, and after the method 200 is repeated using the objectively determined rod position to obtain a more accurate ball center position, the method 600 may be repeated (at least one time) using the updated ball center position to obtain a more accurate rod position. In other embodiments, the method 600 may not need to be repeated. In such cases, the rod position determined from item 604 the first time around may be used as the final rod position.

In further embodiments, the method 200 for determining ball center position, and the method 600 for determining rod position may be repeated multiple times. Each time the method 600 is performed, the method 600 uses the most recent determined ball center position to obtain an updated rod position. Also, each time the method 200 is performed, the method 200 uses the most recent determined rod position to obtain an updated ball center position. The methods 200, 600 may be repeated until a solution is converged. For example, in some embodiments, the method 600 may be repeated multiple times until a difference between two successively determined rod positions falls below a prescribed threshold. Similarly, in another example, in some embodiments, the method 200 may be repeated multiple times until a difference between two successively determined ball center positions falls below a prescribed threshold.

Figure 8:
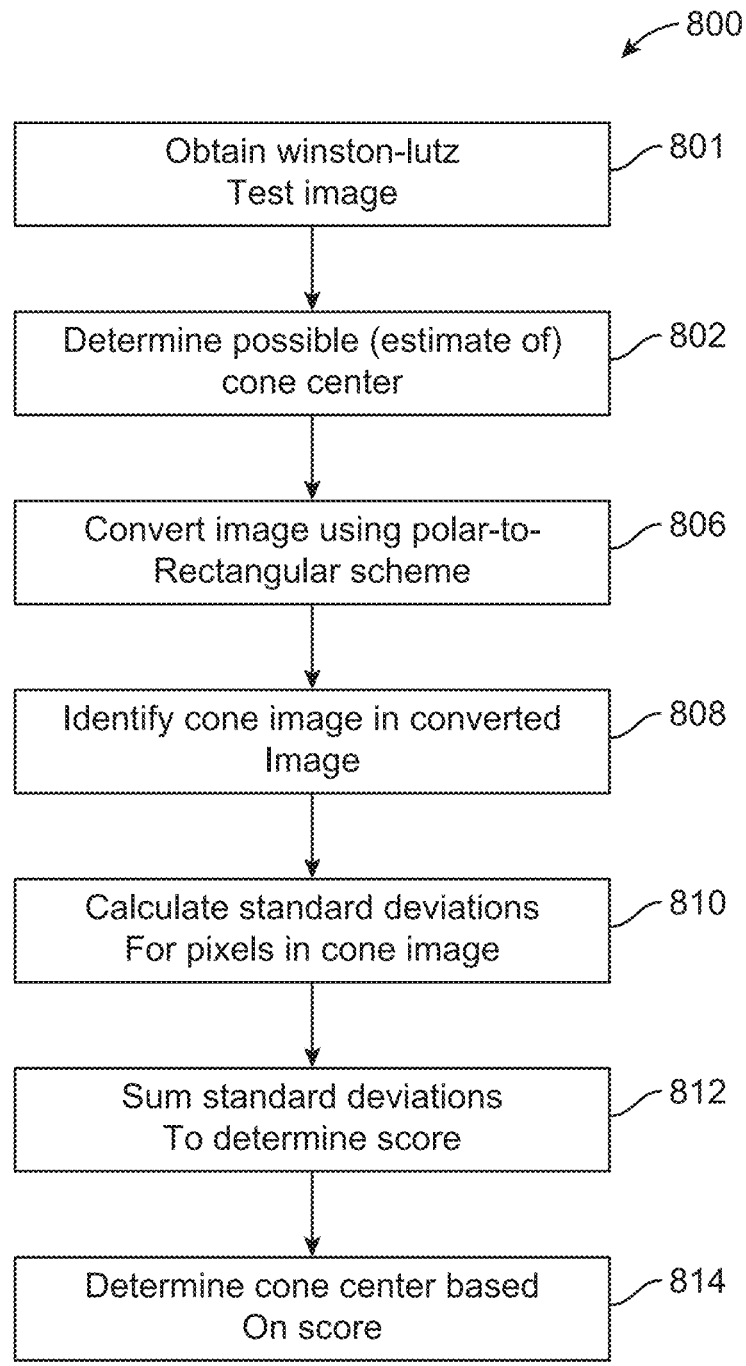
FIG. 8 illustrates a method for determining a center of a cone involved in a Winston-Lutz Test.

In some embodiments, after the final ball center position is determined (either the first time around from item 214, or after repeating the method 200 one or more times), the center of the cone 154 in the image 300 may be determined. In some embodiments, the method of determining the cone center may be similar to the method 200 that was used to determine the ball center. FIG. 8 illustrates a method 800 of determining the center of the cone 154 in accordance with some embodiments.

First, an image of a Winston-Lutz test is obtained (Item 801). An example of the digitized image 300 of Winston-Lutz test is shown in FIG. 3. As shown in the figure, the image 300 includes an image 304 of the ball 152, an image 306 of the cone 154 (i.e., showing the boundary of the circular opening provided by the cone 154), and an image 308 of the rod that is connected to the ball. The image 300 also includes an area 310 representing unobstructed radiation that reaches the detector 106. Since the radiation not blocked by the ball 152 and the cone 154 will reach the detector 106, the area 310 formed by such radiation will have a color or greyscale that is distinctly different from the ball image 304 and the cone image 306. As shown in the figure, the ball image 304 is circular because the ball 152 is spherical in shape, or is as nearly perfectly round as possible. Similarly, the cone image 306 is circular because the opening of the cone 154 is circular, or is as nearly perfectly round as possible. In some embodiments, the act of obtaining the Winston-Lutz test image is performed by a processor receiving the image data of the Winston-Lutz test. In other embodiments, the act of obtaining the Winston-Lutz test image may also include generating the Winston-Lutz test image.

Returning to FIG. 8, next, a possible cone center is determined (Item 802). In some embodiments, a user may manually select a point near the center pixel of the cone image 306 in the image 300 acquired from the Winston-Lutz test. The initial guess of the center of the cone 154 may be input manually by the user as a coordinate (x, y). In some embodiments, the act of determining the possible center in item 702 may be performed by the processor receiving input from the user regarding the initial guess of the cone center. In other embodiments, the initial guess may be automatically determined by the processor, which analyzes the image to make an initial guess of the cone center.

Next, the image 300 is converted to a converted image using a polar to rectangular scheme, similar to a Mercator projection, based on the previously designated coordinate of the initially selected center (Item 806). An example of the converted image 400 that is converted from polar coordinate to rectangular coordinate based on the selected ball center is shown in FIG. 4. The converted image 400 includes an image 304 of the ball 152 expressed in rectangular coordinate, and an image 306 of the cone 154 also expressed in rectangular coordinate. The converted image 400 also includes the area 310 representing unobstructed radiation detected by the detector 106. In some embodiments, the act of converting the image 300 to the converted image 400 may be performed by the processor. Also, in some embodiments, the act of converting the image 300 to the converted image 400 may be performed automatically by the processor.

In some embodiments, the zone/image 308 of the rod may be omitted or discarded when converting the image 300 to the converted image 400. In one implementation, the position of the rod image 308 may be obtained from item 604 in the method 600 if the method 600 was already performed. In other embodiments, if the method 600 has not been performed, the position of the rod image 308 may be estimated and input manually to the processor. In other embodiments, the processor may automatically estimate the position of the rod image 308 by performing image analysis on the image 300/400. It is desirable to discard the rod image 308 from the converted image 400 because doing so will result in the cone image 306 being easier to be identified in the converted image 400. In some embodiments, the identification of the rod image 308 may be achieved by identifying a rod angle, which is the angle in the polar coordinate at which the rod image 308 lies. In other embodiments, the identification of the rod image 308 may be achieved by identifying a horizontal position in the converted image 400 at which the center of the rod image 308 lies.

Next, the image 306 of the cone 154 is identified in the converted image 400 (Item 808). In some embodiment, because the area 310 has a color or darkness that is distinguishable from that of the image 306 of the cone 154, the image 306 of the cone 154 may be identified based on the difference in the color or darkness between the regions 306, 310. For example, the processor may select all of the pixels below the area 310 that have a color or darkness different (e.g., with the difference being above a certain prescribed threshold) from that in the area 310 as the image pixels for the cone 154. In some embodiments, the identification of the image 306 that corresponds with the cone 154 in the converted image 400 may be performed using the processor. Also, in some embodiments, the identification of the image 306 that corresponds with the cone 154 may be performed automatically by the processor.

Next, the standard deviation for the plurality of pixel rows of the zone 306 wherein the cone 154 lies (the portion 306 in the converted image 400) is calculated (Item 810). In the illustrated embodiments, the standard deviation is calculated row-by-row, and so there are multiple standard deviation values for the respective rows. In some embodiments, the calculation of the standard deviation may be performed by the processor. Also, in some embodiments, the calculation of the standard deviation may be performed automatically by the processor.

Next, the row-wise standard deviation values are summed up to obtain an eccentricity score (Item 812). The eccentricity score represents how well the estimate (e.g., (x, y)) lies in the actual center of the cone image 306. In some embodiments, the eccentricity score may represent the eccentricity of the determined cone center (i.e., an amount of difference between the determined cone center and the actual cone center), wherein a lower score represents less eccentricity, and therefore, a more accurate estimate. In other embodiments, the eccentricity score also represent the quality of the image data, which may indicate possible malfunction(s) in the Clinac operation. In some embodiments, item 812 may be performed by the processor. Also, in some embodiments, item 812 may be performed by the processor automatically.

Next, the center of the cone 154 is determined based at least in part on the eccentricity score (item 814). In some embodiments, the above algorithm may be repeated with one or more cone center estimate(s) to obtain one or more corresponding eccentricity score(s). The cone center estimate with the lowest corresponding eccentricity score is then selected as the center of the cone 154. In some embodiments, a determined eccentricity score may be used to determine a next estimate of the center of the cone 154. Also, in some embodiments, an optimization algorithm may be employed by the processor to minimize the eccentricity score, to thereby find the optimized/actual center of the cone 154 in the image. When the actual center of the cone 154 is determined, or the eccentricity score is minimized, the converted image 400 converted from the image 300 based on the determined actual cone center will show the image 306 for the cone 154 having an uniform shape. In some embodiments, item 814 may be performed by the processor. Also, in some embodiments, item 814 may be performed by the processor automatically.

In some embodiments, the determined center of the cone 154 from item 814 may be stored in a non-transitory medium for later use or processing.

Figure 9:
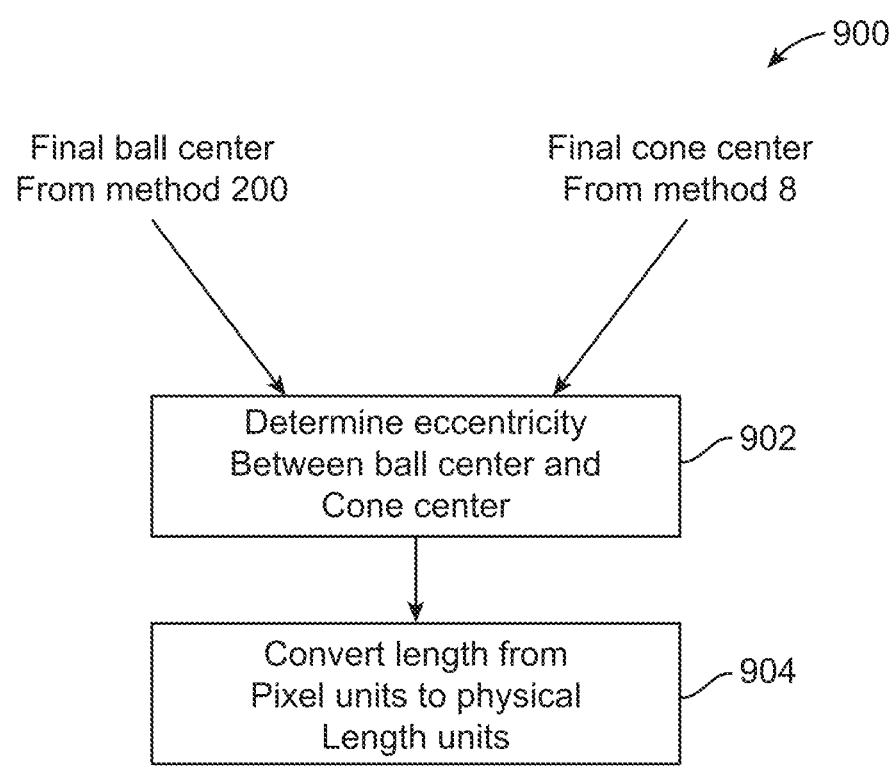
FIG. 9 illustrates a method for determining an eccentricity between a ball center and a cone center.
Figure 10:
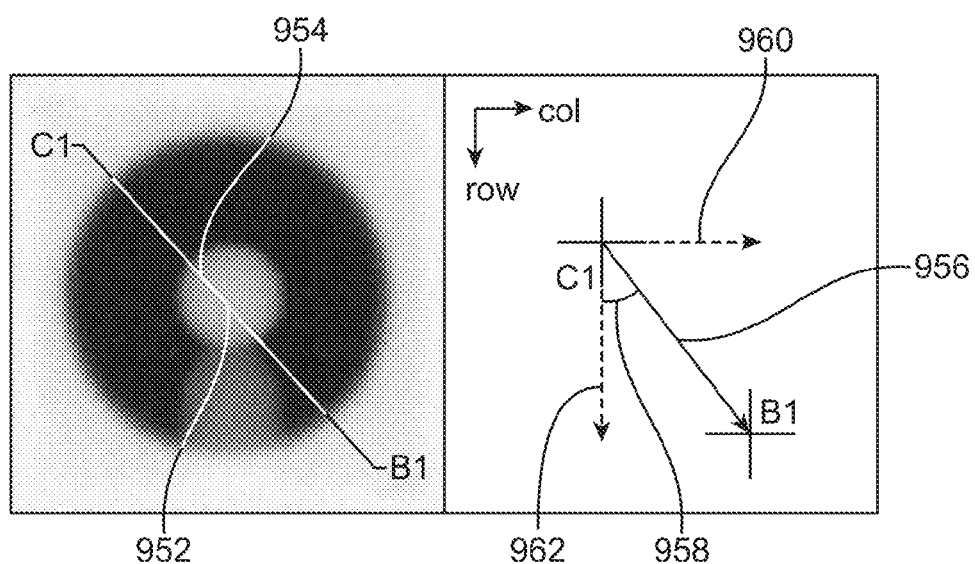
FIG. 10 illustrates an example of an eccentricity between a ball center and a cone center.

In some embodiments, as shown in the method 900 of FIG. 9, after the final ball center has been determined from method 200, and after the final cone center has been determined from method 800, the processor may then calculate an eccentricity (distance and angle) between the ball center and the cone center (Item 902). FIG. 10 illustrates the eccentricity between the ball center and the cone center. In the illustrated example, the determined ball center is at location 952, and the determined cone center is at location 954. The offset distance between the ball center and the cone center is represented by distance 956, and the angle (direction of offset) is represented by angle 958. The distance 956 may be represented by x-component 960 and y-component 962. In some embodiments, the processor may calculate such eccentricity automatically. In some embodiments, the distance component of the eccentricity vector (e.g., distance and angle between the cone and ball centers) may be expressed in pixel values. In one implementation, the difference in distance between the ball center and cone center may be expressed in row-column space coordinates, of which row corresponds to y-axis and column corresponds to the x-axis. In some embodiments, the length (offset) component of the eccentricity vector may optionally be converted from pixel units to physical length units (e.g., millimeters) (item 904). The final results are the precise calculation of ball center location, cone center location, the distance offset between the ball center and cone center, and the direction of offset between the ball center and cone center, for the particular image 300 taken at a certain gantry angle. In some embodiments, these results may be stored in a non-transitory medium for later use.

The above methods are described with reference to a certain image 300 generated while the detector 106 is at a certain gantry angle. In some embodiments, the above methods (e.g., method 200, method 600, method 800, and method 900) may be repeated to obtain multiple images 300 at different respective gantry angles. In such cases, the final results are ball center locations, cone center locations, offset directions between the respective ball center locations and cone center locations, and directions of offset between the respective ball centers and cone centers, for the respective images 300 at the different gantry angles.

Also, in some embodiments, for each of the selected N gantry angles, the collimator may be rotated to M different positions, and M different test images may be obtained for the M different positions. In such cases, there will be N×M number of test images. The above described technique, which is for processing one test image, may be performed for one of the N×M images to obtain an eccentricity score between the cone center and the ball center for a particular image. In addition, in some embodiments, the technique of finding the ball center, cone center, and centerline of rod may be repeated multiple times until the best ball center, best cone center, and best rod centerline is achieved. In some embodiments, once the best rod centerline is obtained, the ball center may be obtained. Also, once the best ball center is obtained, the best cone center may be obtained. Thus, the best center of each component may be obtained by using one best center after another, in order to arrive at the best eccentricity score between the cone center and the ball center.

The above embodiments of the image processing methods are advantageous. They automate the determination of the precise location of the ball center and cone center based on the digital image acquired during Winston-Lutz test. The embodiments of the methods are objectively precise, immune to short scale noise and penumbra, check for malfunction or calibration drift (long scale noise), may be automated, provide faster determination (e.g., compared to autocorrelation technique) of geometric position, and provide geometric position determination with higher accuracy when compared to the conventional method of using visual estimation and ruler to measure the isocenter. In some cases, the precision may be at least $1/100^{th}$ of a pixel. In some cases, embodiments of the methods described herein may also provide compensation factors to correct image shift error due to X-ray source deviations and imager panel mechanical shift, which may include gravity, positioning error, gantry bearing error, or similar disturbances.

It should be noted that the technique for determining ball center and the technique for determining cone center is not limited to the examples described previously.

In some embodiments, different eccentricity scores may be obtained for different respective gantry angles. For example, N different gantry angles may be prescribed, and there may be N corresponding eccentricity scores. In such cases, the N eccentricity scores may be combined or used together to obtain a final eccentricity between the ball center and the cone center. Such feature will be described in further detail below.

Figure 11:
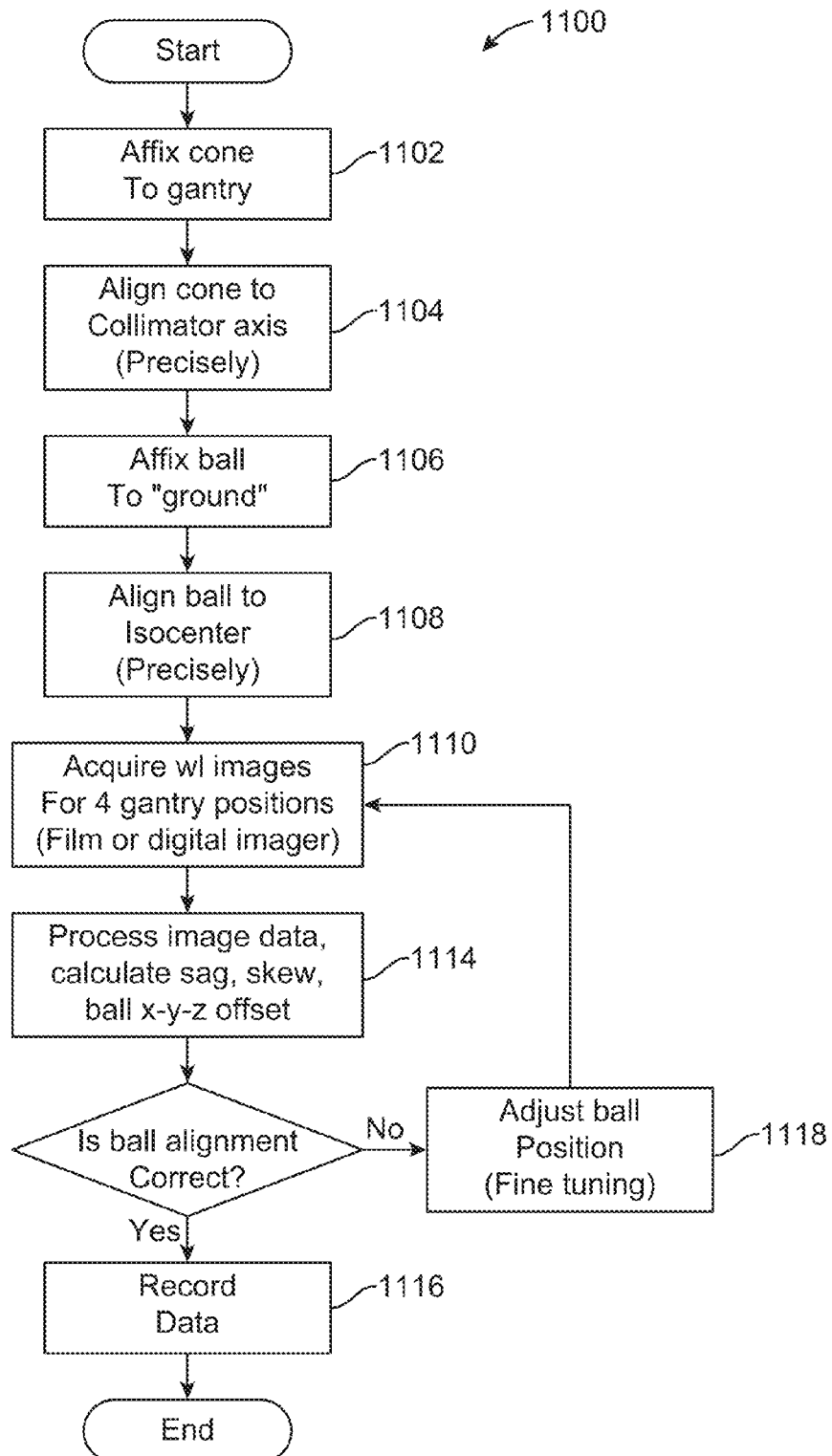
FIG. 11 illustrates a method for ball alignment.

One embodiment of the present image processing algorithm may determine isocenter sag (e.g., the deviation from isocenter along the Y-axis) and skew (e.g., the deviation from the isocenter along the X-axis) errors for purpose of ball alignment. FIG. 11 illustrates a method 1100 for ball alignment that involves determination of sag and skew errors, and ball center offsets. First, the cone 154 is affixed to the gantry (Item 1102), and the cone 154 is then aligned to the collimator axis (Item 1104). Next, the ball 152 is attached to a reference structure, such as a patient support (Item 1106), and the ball 152 is aligned to isocenter (Item 1108).

Next Winston-Lutz test images are obtained (Item 1110). At a minimum, two Winston-Lutz test images are obtained. However, in the illustrated embodiments, four Winston-Lutz test images are obtained at four respective angles $\theta_1$, $\theta_2$, $\theta_3$, and $\theta_4$ (e.g., at 0°, 90°, 180°, and 270°), and the ball center, cone center, and eccentricity between the ball center and cone center are determined to determine ball offset for each image (Item 1114). SAG and SKEW may also be determined in item 1114. In the illustrated examples, the four gantry angles correspond to head up, down, and two sides positions. In other embodiments, there may be more than four Winston-Lutz test images or fewer than four Winston-Lutz test images. In some embodiments, the eccentricities (ball center offsets) may be determined using the methods 200, 600, 800, and 900 for the respective images taken at the respective gantry angles. If the ball 152 is aligned to isocenter with sufficient precision (e.g., ball offset is less than a prescribed threshold), the data (including SAG info, SKEW info, ball center location, cone center location, and eccentricity for each of the gantry angels) is recorded in a non-transitory medium (Item 1116), and the method 1100 is completed. If the ball 152 is not aligned to isocenter with sufficient precision, the ball 152 is manually adjusted (Item 1118) and Items 1110, 1112 shown in FIG. 11 are repeated until the ball is aligned accurately to the isocenter.

In some embodiments, the eccentricity values (vectors) may be used to calculate sag, skew, and ball x-y-z offset. The calculation of sag, skew, and ball x-y-z offsets may be performed as follows:

$$sag = \frac{ecc_{row}(0) - ecc_{row}(180)}{2}$$

where $ecc_{row}(0)$ is the row component of the eccentricity vector for the "head down" position, and $ecc_{row}(180)$ is the row component of the eccentricity vector for the "head up" position.

$$skew = \frac{ecc_{col}(0) + ecc_{col}(180)}{2}$$

where $ecc_{col}(0)$ is the column component of the eccentricity vector for the "head down" position, and $ecc_{col}(180)$ is the column component of the eccentricity vector for the "head up" position.

$$x\_offset = \frac{ecc_{col}(0) - ecc_{col}(180)}{2}$$
$$y\_offset = \frac{ecc_{row}(0) + ecc_{row}(90) + ecc_{row}(180) + ecc_{row}(270)}{4}$$
$$z\_offset = \frac{ecc_{col}(90) - ecc_{col}(270)}{2}$$

where $(ecc_{row}(90)$ is the row component of the eccentricity vector for the $\theta_2=90°$, $(ecc_{row}(270)$ is the row component of the eccentricity vector for the $\theta_4=270°$, $(ecc_{col}(90)$ is the column component of the eccentricity vector for the $\theta_2=90°$, and $(ecc_{row}(270)$ is the column component of the eccentricity vector for the $\theta_4=270°$.

In other embodiments, $\theta_1$, $\theta_2$, $\theta_3$, and $\theta_4$ may have other values. In such cases, the above equations still apply, and $ecc_{col}(0)$, $ecc_{col}(90)$, $ecc_{col}(180)$, $ecc_{col}(270)$, $ecc_{row}(0)$, $ecc_{row}(90)$, $ecc_{row}(180)$, and $ecc_{row}(270)$ will be replaced with the $ecc_{col}(\theta_1)$, $ecc_{col}(\theta_2)$, $ecc_{col}(\theta_3)$, $ecc_{col}(\theta_4)$, $ecc_{row}(\theta_1)$, $ecc_{row}(\theta_2)$, $ecc_{row}(\theta_3)$, and $ecc_{row}(\theta_4)$, respectively.

In some embodiments, different eccentricity scores may be obtained for different respective gantry angles. For example, N different gantry angles may be prescribed, and there may be N corresponding eccentricity scores. Also, for each of the N gantry angles, the collimator may be prescribed to be rotated to M different collimator positions for obtaining M different respective test images. Thus, there may be N×M test images, which may be used to obtain a final eccentricity between the ball center and the cone center. Such feature will be described in further detail below.

Figure 12:
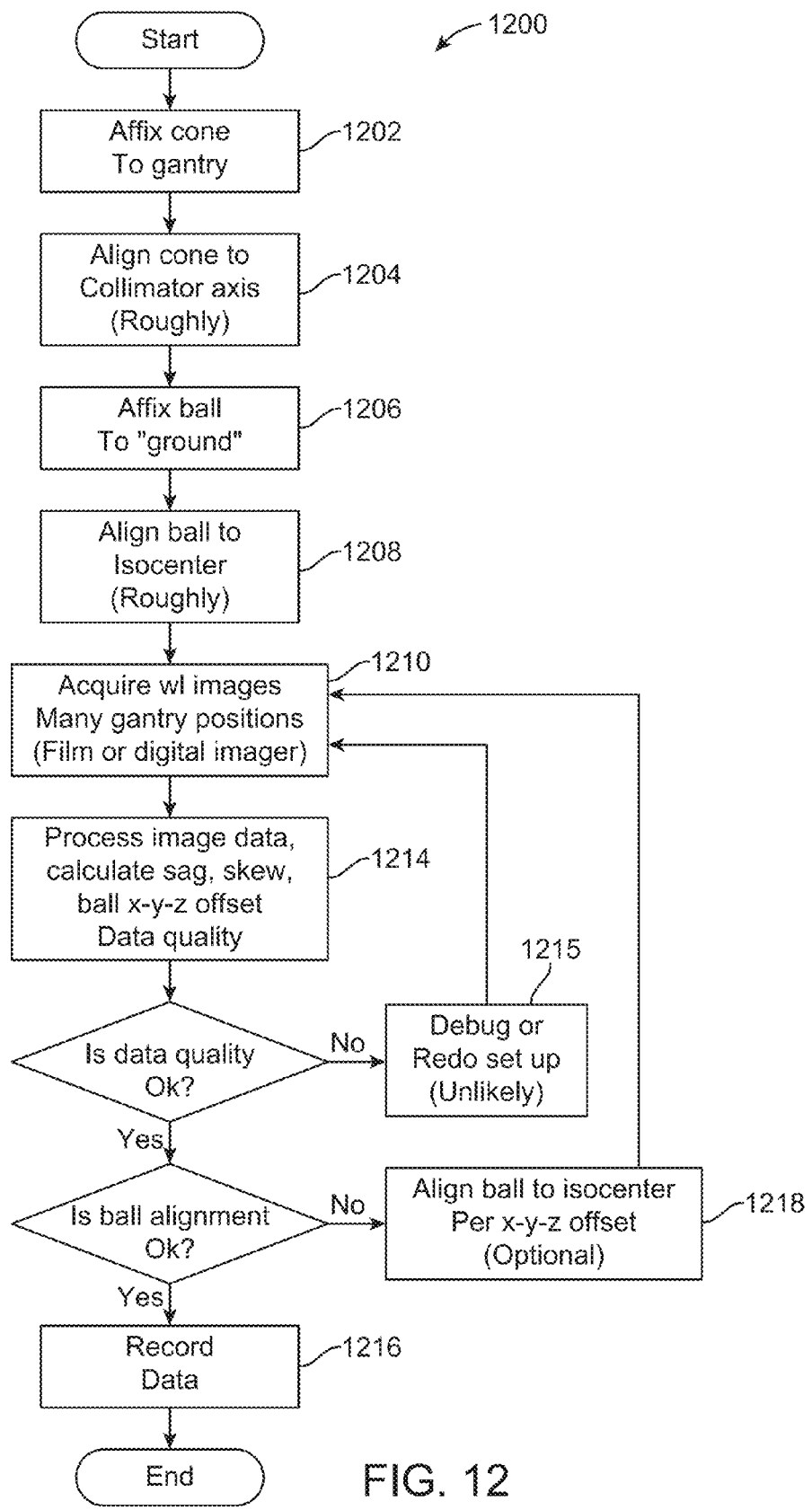
FIG. 12 illustrates another method for ball alignment.

Another embodiment of the present image processing algorithm may determine sag, skew, ball center x-y-z offsets from cone center, data quality, and image panel shift, which may be used for ball alignment and radiation system setup. FIG. 12 illustrates a method 1200 for ball alignment. First, the cone 154 is affixed to the gantry (Item 1202), and the cone 154 is then aligned to the collimator axis, e.g., to an accuracy of +/−0.05 inch (Item 1204). Next, the ball 152 is attached to a reference structure, such as a patient support (Item 1206), and the ball 152 is aligned to isocenter, e.g., to an accuracy of +/−0.05" (Item 1208).

Next Winston-Lutz test images are obtained (Item 1210). At a minimum, two Winston-Lutz test images are obtained. In the illustrated embodiments, N×M Winston-Lutz test images are obtained, where N is the number of different gantry angles that may be arbitrarily selected from within a range of gantry motion, and M is the number of collimator positions that may be arbitrarily selected from within a range of motion. In some embodiments, the N different gantry angles may be 0, 30, 60, 90, 120, 150, 180, 210, 240, 270, 300, 330, 360 degrees, for examples. Also, in some embodiments, the M different collimator positions may be 45, 75, 105, 135, 165, 195, 225, 255, 285, 315, 345 degrees, for examples. In one implementation, at each of the N gantry angles, M Winston-Lutz test images are obtained for the N different collimator positions. This is repeated for all of N gantry angles to obtain the N×M Winston-Lutz test images.

Next, eccentricity (ball offset) between the ball center and cone center are determined for each selected gantry angle θ (Item 1214). SAG, SKEW, data quality info (measurement quality), and imager panel shift information, may also be determined in item 1214. The data quality information indicates a quality of the measurement taken.

Figure 13:
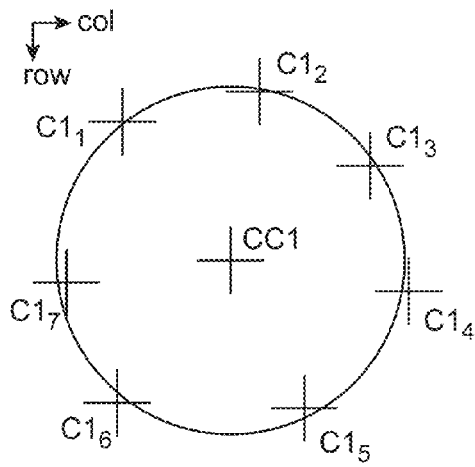
FIG. 13 illustrates a concept of center of circle.

In some embodiments, the ball center positions (B1) and cone center positions (C1) may be determined for each of the selected gantry angles. Such may be performed using known techniques, or the techniques described with reference to methods 200, 600, and 800. An additional parameter, CC1, may be calculated, which is the center of the circle generated from a group of cone center positions C1's associated with a certain gantry position (FIG. 13). In one implementation, CC1 for each gantry position θ may be determined by finding the center of a circle generated by the cone centers of a group of images taken at a particular gantry position θ (e.g., images taken at a particular gantry position θ as the collimator rotates through the M different selected collimator positions $\beta_1$-$\beta_M$). The above may be repeated for the rest of the N selected gantry angles. In some embodiments, C1, B1, and CC1, may be expressed in row-column space coordinates.

In the illustrated embodiments, after CC1's have been determined for the different gantry angles, the values of the CC1 may then be used to determine ball offsets, SAG, SKEW, data quality info, and imager panel shift information.

In other embodiments, the eccentricities (ball offsets) may be determined using the methods 200, 600, 800, and 900 for the respective gantry angles θ.

As shown in FIG. 12, if the measurement quality is acceptable, the method 1200 then determines whether the ball 152 is aligned with sufficient precision. If the measurement quality is not acceptable, then a debug and/or setup process is performed (Item 1215) until the measurement quality is acceptable.

If the ball 152 is aligned to isocenter with sufficient precision, the data (including data quality information, panel shift information, SAG info, SKEW info, ball center location, cone center location, and eccentricity for each of the gantry angels) is recorded in a non-transitory medium (Item 1216), and the method is completed. If the ball 152 is not aligned to isocenter with sufficient precision, the ball 152 is manually adjusted (Item 1218) and the Items 1210, 1214 are repeated until the ball 152 is aligned with sufficient accuracy to the isocenter.

Figure 14:
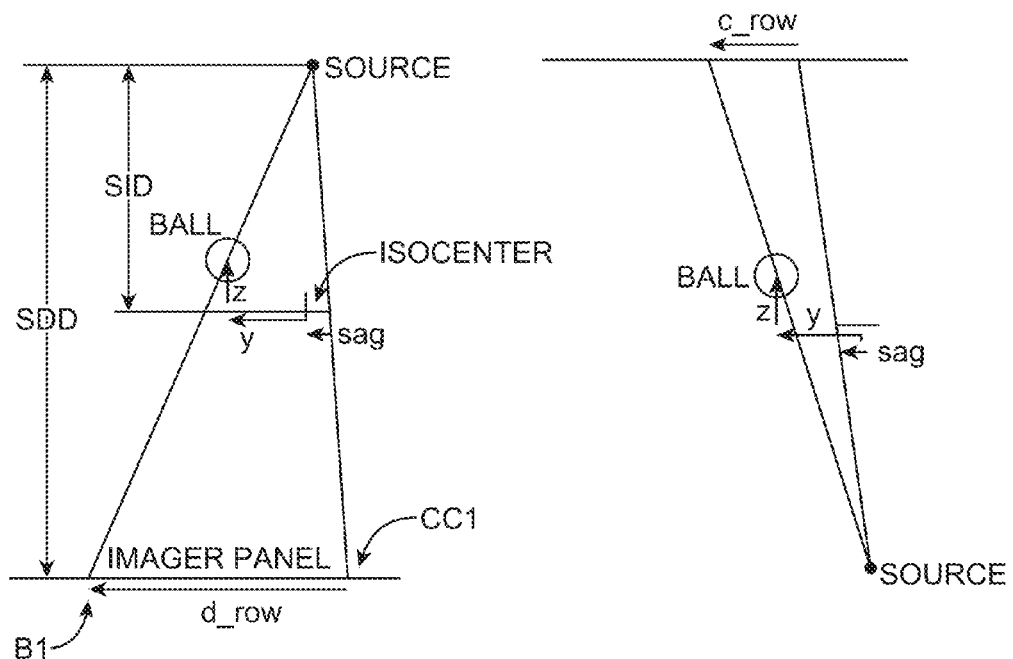
FIG. 14 illustrates a side view of a radiation system with definitions for SAG and ball-isocenter Y-offset calculation.

In some embodiments, the isocenter sag, the ball-isocenter Y-offset and Measurement Quality may be calculated by the following relationships (see FIG. 14):

(1) For each gantry position θ, the ball-cone distances $d\_row(\theta)$ in the image row-direction are calculated from:

$$d\_row(\theta) = B1_{row}(\theta) - CC1_{row}(\theta)$$

(2) The sag and ball Y-offset are calculated by best-fitting the relation:

$$d\_row(\theta) = \frac{SDD}{SID} \cdot (Y\_offset - sag \cdot \cos(\theta))$$

by optimizing the parameters Y_offset and sag. In the above relationship, SDD=distance from the radiation source to the image panel, and SID=distance from the radiation source to the isocenter.

(3) The Measurement Quality, σ_sag, of sag and Y-offset is the standard deviation of the residual errors between each measure and best-fit function, per gantry angle:

$$\sigma\_sag = \sqrt{\frac{1}{N} \cdot \sum_{\theta=1}^{N} \left[ d\_row(\theta) - \frac{SDD}{SID} \cdot (Y\_offset - sag \cdot \cos(\theta)) \right]^2}$$

Low values for σ_sag indicate a better conformance of data to the optimized function than that associated with high values of σ_sag. Values of σ_sag less than 100 microns (for example) may indicate valid data.

Figure 15:
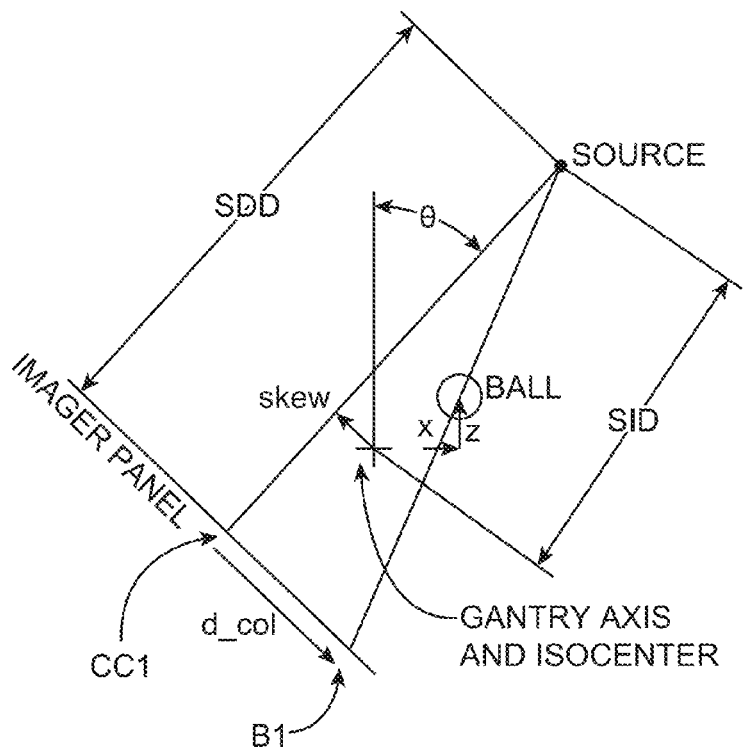
FIG. 15 illustrates a front view of a radiation system with definitions for SKEW, ball-isocenter X-offset and Z-offset calculation.

Also, in some embodiments, the isocenter skew, the ball-isocenter X- and Z-offsets, and Measurement Quality may be calculated by the following relationships (see FIG. 15):

(1) For each gantry position θ, the ball-cone distances $d\_col(\theta)$ in the image col-direction are calculated from:

$$d\_col(\theta) = B1_{col}(\theta) - CC1_{col}(\theta)$$

(2) The skew and ball X-offset and ball Z-offset are calculated by best fitting the relation (e.g., by optimizing the parameters skew, X-offset, and Z-offset):

$$d\_col(\theta) = \left(\frac{SDD}{SID}\right) \cdot (skew + X\_offset \cdot \cos(\theta) - Z\_offset \cdot \sin(\theta))$$

to the parameters X-offset, Z-offset and skew (e.g., by optimizing the parameters skew, X-offset, and Z-offset). In the above relationship, SDD=distance from the radiation source to the image panel, and SID=distance from the radiation source to the isocenter.

(3) The Measurement Quality, σ_askew, of skew, X-offset and Z-offset is the standard deviation of the residual errors between each measure and best-fit function, per gantry angle:

$$\sigma\_skew = \sqrt{\frac{1}{N} \cdot \sum_{\theta=1}^{N} \left[ d\_col(\theta) - \left(\frac{SDD}{SID}\right) \cdot (skew + X\_offset \cdot \cos(\theta) - Z\_offset \cdot \sin(\theta)) \right]^2}$$

Low values for σ_askew indicate a better conformance of data to the optimized function than that associated with high values of σ. Values of σ_skew less than 100 microns (for example) may indicate valid data.

Figure 16:
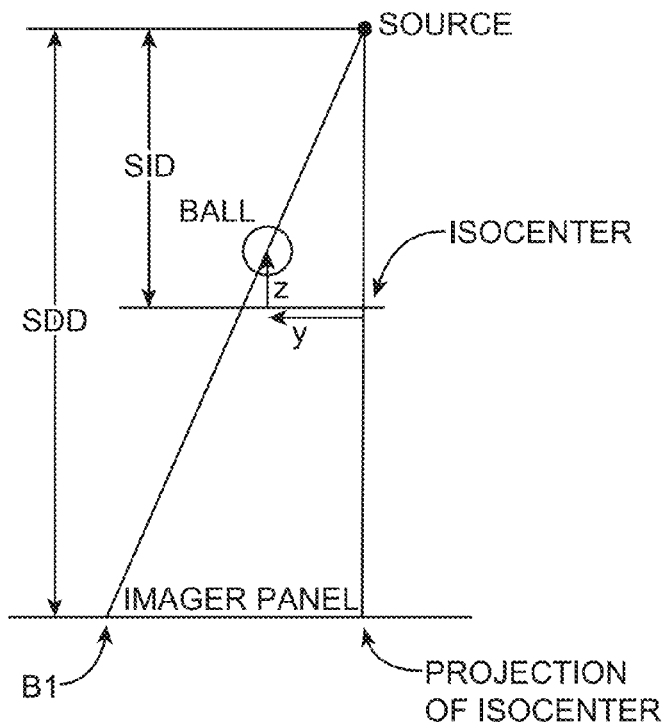
FIG. 16 illustrates a side view of projection of isocenter onto imager panel.

The location of isocenter projection on the imager panel (which constitutes effective imager panel shift) may calculated based on the following:

(1) For each gantry position θ, the projection of isocenter on the panel is, in the row-direction (FIG. 16):

$$ISO_{row}(\theta) = B1_{row}(\theta) - \left(\frac{SDD}{SID}\right) \cdot Y\_offset$$

Figure 17:
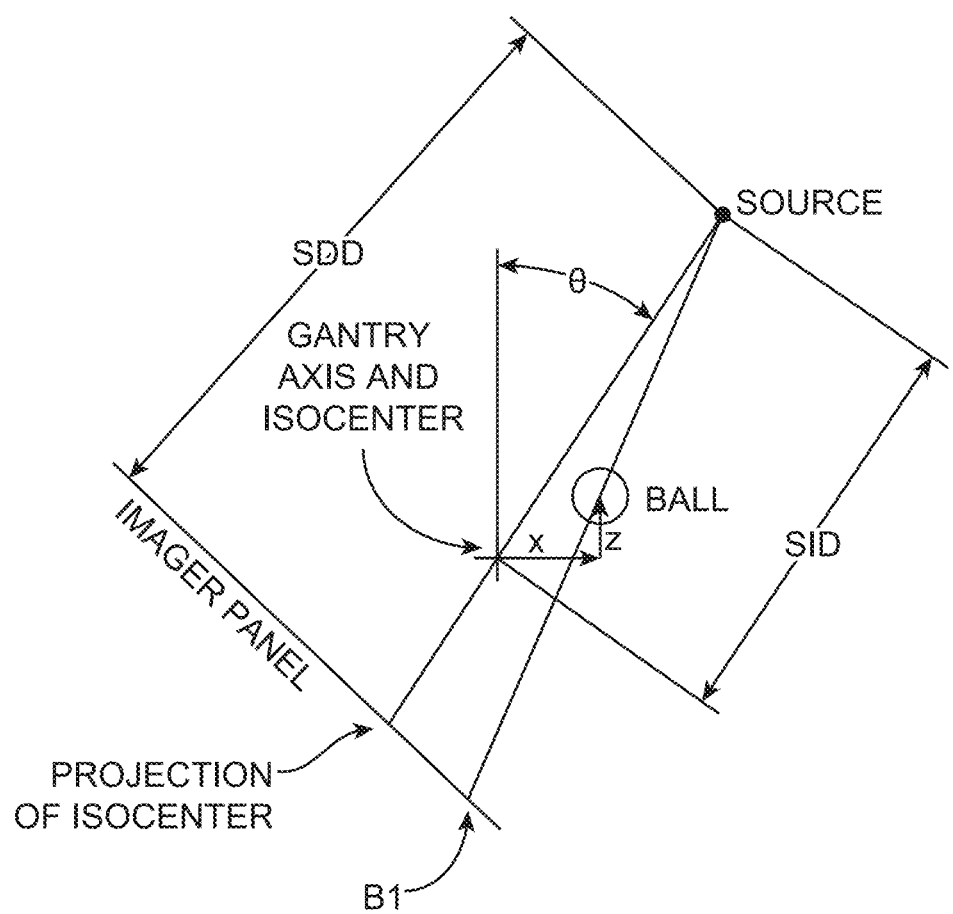
FIG. 17 illustrates a front view of projection of isocenter onto imager panel.

(2) For each gantry position θ, the projection of isocenter on the panel is, in the col-direction (FIG. 17):

$$ISO_{col}(\theta) = B1_{col}(\theta) - \left(\frac{SDD}{SID}\right) \cdot (X\_offset \cdot \cos(\theta) - Z\_offset \cdot \sin(\theta))$$

The above technique is advantageous because it eliminates the requirement to precisely mechanically position the cone 154 to achieve alignment with the collimator rotation axis. By doing so, expenditure of skilled manual labor will be saved in addition to eliminating errors arising from imperfect mechanical alignment. Also, the above technique calculates data quality, which averts the problem of unexpected measurement uncertainty from corrupting calculated values of sag, skew, and ball x-y-z offset (but not imager panel shift). The above technique also provides the projection of isocenter onto the imager panel, which may be used as compensation factors to correct image shift error due to X-ray source deviations due to sag and/or skew, and due to imager panel mechanical shift due to gravity, positioning error, gantry bearing error, or similar disturbances.

Computer Architecture

Figure 18:
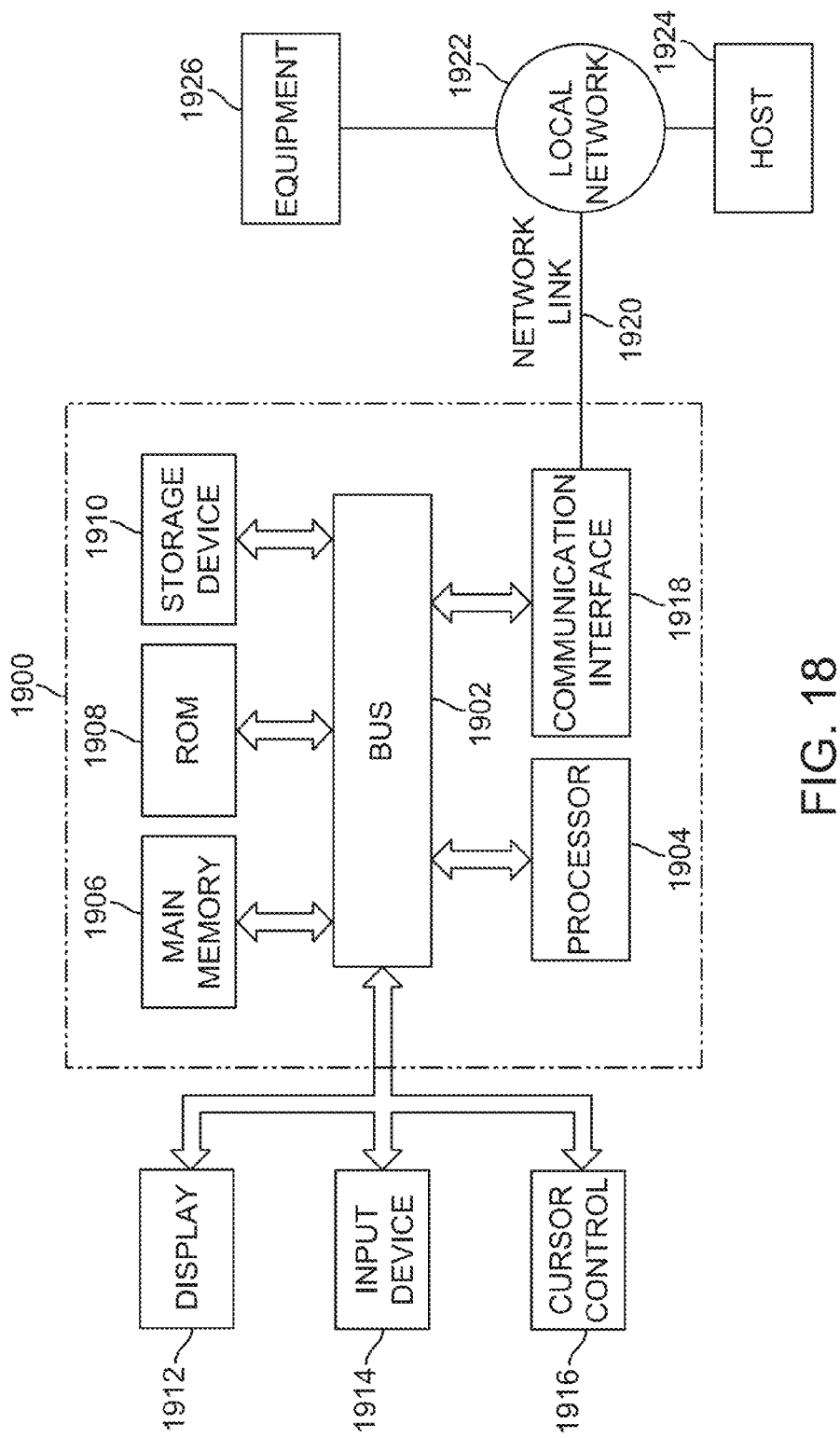
FIG. 18 illustrates an example of a computer architecture with which embodiments described herein may be implemented.

FIG. 18 is a block diagram that illustrates an embodiment of a computer system 1900 upon which one or more embodiments described herein may be implemented. For example, in some embodiments, the computer system 1900 may be configured to perform the method 200, method 600, method 700, or any combination of the foregoing. Computer system 1900 includes a bus 1902 or other communication mechanism for communicating information, and a processor 1904 coupled with the bus 1902 for processing information. The processor 1904 may be a part of a radiation system, or another processor that is used to perform various functions described herein. In some cases, the computer system 1900 may be used to implement the processor 14 (or other processors described herein).

The computer system 1900 also includes a main memory 1906, such as a random access memory (RAM) or other dynamic storage device, coupled to the bus 1902 for storing information and instructions to be executed by the processor 1904. The main memory 1906 also may be used for storing temporary variables or other intermediate information during execution of instructions to be executed by the processor 1904. The computer system 1900 further includes a read only memory (ROM) 1908 or other static storage device coupled to the bus 1902 for storing static information and instructions for the processor 1904. A data storage device 1910, such as a magnetic disk or optical disk, is provided and coupled to the bus 1902 for storing information and instructions.

The computer system 1900 may be coupled via the bus 1902 to a display 1912, such as a cathode ray tube (CRT) or a flat panel, for displaying information to a user. An input device 1914, including alphanumeric and other keys, is coupled to the bus 1902 for communicating information and command selections to processor 1904. Another type of user input device is cursor control 1916, such as a mouse, a trackball, or cursor direction keys for communicating direction information and command selections to processor 1904 and for controlling cursor movement on display 1912. This input device typically has two degrees of freedom in two axes, a first axis (e.g., x) and a second axis (e.g., y), that allows the device to specify positions in a plane.

The computer system 1900 may be used for performing various functions (e.g., calculation) in accordance with the embodiments described herein. According to one embodiment, such use is provided by computer system 1900 in response to processor 1904 executing one or more sequences of one or more instructions contained in the main memory 1906. Such instructions may be read into the main memory 1906 from another computer-readable medium, such as storage device 1910. Execution of the sequences of instructions contained in the main memory 1906 causes the processor 1904 to perform the process steps described herein. One or more processors in a multi-processing arrangement may also be employed to execute the sequences of instructions contained in the main memory 1906. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 1904 for execution. Such a medium may take many forms, including but not limited to, non-volatile media, volatile media, and transmission media. Non-volatile media includes, for example, optical or magnetic disks, such as the storage device 1910. A non-volatile medium may be considered as an example of a non-transitory medium. Volatile media includes dynamic memory, such as the main memory 1906. A volatile medium may be considered as another exampler of a non-transitory medium. Transmission media includes coaxial cables, copper wire and fiber optics, including the wires that comprise the bus 1902. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1904 for execution. For example, the instructions may initially be carried on a magnetic disk of a remote computer. The remote computer can load the instructions into its dynamic memory and send the instructions over a telephone line using a modem. A modem local to the computer system 1900 can receive the data on the telephone line and use an infrared transmitter to convert the data to an infrared signal. An infrared detector coupled to the bus 1902 can receive the data carried in the infrared signal and place the data on the bus 1902. The bus 1902 carries the data to the main memory 1906, from which the processor 1904 retrieves and executes the instructions. The instructions received by the main memory 1906 may optionally be stored on the storage device 1910 either before or after execution by the processor 1904.

The computer system 1900 also includes a communication interface 1918 coupled to the bus 1902. The communication interface 1918 provides a two-way data communication coupling to a network link 1920 that is connected to a local network 1922. For example, the communication interface 1918 may be an integrated services digital network (ISDN) card or a modem to provide a data communication connection to a corresponding type of telephone line. As another example, the communication interface 1918 may be a local area network (LAN) card to provide a data communication connection to a compatible LAN. Wireless links may also be implemented. In any such implementation, the communication interface 1918 sends and receives electrical, electromagnetic or optical signals that carry data streams representing various types of information.

The network link 1920 typically provides data communication through one or more networks to other devices. For example, the network link 1920 may provide a connection through local network 1922 to a host computer 1924 or to equipment 1926 such as a radiation beam source or a switch operatively coupled to a radiation beam source. The data streams transported over the network link 1920 can comprise electrical, electromagnetic or optical signals. The signals through the various networks and the signals on the network link 1920 and through the communication interface 1918, which carry data to and from the computer system 1900, are exemplary forms of carrier waves transporting the information. The computer system 1900 can send messages and receive data, including program code, through the network(s), the network link 1920, and the communication interface 1918.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. For example, the term "image" needs not be limited to an image that is displayed visually, and may refer to image data that is stored. Also, the term "processor" may include one or more processing units, and may refer to any device that is capable of performing mathematical computation implemented using hardware and/or software. The term "processor" may also refer to software stored in a non-transitory medium in other embodiments. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed is:

1. An image processing method, comprising:
obtaining an image that includes a ball image and a cone image, wherein the ball image indicates an image of a ball, and the cone image indicates an image of a cone;
converting the image to a converted image using a processor, wherein the converted image comprises a converted ball image that looks different from the ball image in the image, and a converted cone image that looks different from the cone image in the image;
identifying the converted ball image in the converted image;
analyzing the converted ball image to determine a score; and
determining a center of the ball image based at least in part on the score;
wherein the obtained image also includes a rod image, and the method further comprises using the processor to determine a position of the rod image using an algorithm.

2. The method of claim 1, wherein the method further comprises determining a first amount of a first offset in a first direction between a center of the ball and a center of the cone.

3. The method of claim 2, further comprising determining a second amount of a second offset in a second direction between the center of the ball and the center of the cone, the second direction being orthogonal to the first direction.

4. The method of claim 3, further comprising determining a third amount of a third offset in a third direction between the center of the ball and the center of the cone, the third direction being orthogonal to the first direction and the second direction.

5. The method of claim 1, wherein the image is converted to the converted image using a polar-to-rectangular coordinate conversion scheme.

6. The method of claim 1, wherein the converted ball image has a non-circular shape.

7. The method of claim 1, wherein the act of identifying the converted ball image is performed by the processor, which analyzes the converted image to identify a region in which the converted ball image lies.

8. The method of claim 1, wherein the act of analyzing the converted ball image comprises:
calculating standard deviation values for a plurality of respective rows of pixels that correspond to the converted ball image; and
summing the standard deviation values to obtain the score.

9. The method of claim 1, wherein the obtained image also includes a rod image, and the method further comprises identifying the rod image in the obtained image.

10. The method of claim 1, wherein the rod image in the image is excluded before converting the image to the converted image.

11. The method of claim 1, further comprising determining an additional center of the ball image based at least in part on the determined position of the rod, the additional center of the ball image being more accurate than the previously determined center of the ball image.

12. The method of claim 1, further comprising obtaining an estimate of a center of the ball image, wherein the image is converted to a converted image using the processor based at least in part on the estimate of the center of the ball image.

13. The method of claim 12, further comprising:
determining a center of the ball image based at least in part on the score;
determining one or more additional scores for one or more additional estimates of the center of the cone image, wherein the center of the ball image is determined by selecting one of the estimates that has the lowest score.

14. The method of claim 1, further comprising:
determining a center of the ball image based at least in part on the score; and
using the processor to determine a center of the cone image.

15. The method of claim 14, further comprising determining an eccentricity between the determined center of the ball image and the determined center of the cone image.

16. The method of claim 15, wherein the eccentricity comprises an offset distance between the determined center of the ball image and the determined center of the cone image, and a direction of the offset distance.

17. The method of claim 16, wherein the offset distance is expressed in pixel values, and the method further comprises converting the offset distance from pixel values to length units.

18. The method of claim 1, further comprising:
determining a center of the ball image based at least in part on the score; and
using the determined center of the ball image and one or more other parameters to determine one or more of an isocenter sag, isocenter skew, quality data representing measurement quality, and panel shift.

19. The method of claim 1, wherein the score represents an accuracy of an estimate of a center of the ball image.

20. A computer product having a non-transitory medium storing a set of instructions, an execution of which will cause an imaging method to be performed, the method comprising:
obtaining an image that includes a ball image and a cone image, wherein the ball image indicates an image of a ball, and the cone image indicates an image of a cone;
converting the image to a converted image using a processor, wherein the converted image comprises a converted ball image that looks different from the ball image in the image, and a converted cone image that looks different from the cone image in the image;
identifying the converted ball image in the converted image;
analyzing the converted ball image to determine a score; and
determining a center of the ball image based at least in part on the score;
wherein the obtained image also includes a rod image, and the method further comprises determining a position of the rod image using an algorithm.

21. An image processing method, comprising:
obtaining an image that includes a ball image and a cone image;
using a processor to execute a first algorithm to determine a ball center;
using the processor to execute a second algorithm to determine a cone center;
determining an eccentricity between the determined ball center and the determined cone center; and
using the determined ball center and one or more other parameters to determine an isocenter sag, an isocenter skew, quality data representing measurement quality, a panel shift, or any combination of the foregoing;
wherein the first algorithm involves converting the ball image to a converted ball image that looks different from the ball image.

22. The method of claim 21, wherein the ball image indicates an image of a ball, and the cone image indicates an image of a cone, and wherein the method further comprises determining a first amount of a first offset in a first direction between a center of the ball and a center of the cone.

23. The method of claim 22, further comprising determining a second amount of a second offset in a second direction between the center of the ball and the center of the cone, the second direction being orthogonal to the first direction.

24. The method of claim 23, further comprising determining a third amount of a third offset in a third direction between the center of the ball and the center of the cone, the third direction being orthogonal to the first direction and the second direction.

25. The method of claim 21, wherein the eccentricity comprises an offset distance between the determined ball center and the determined cone center, and a direction of the offset distance.

26. The method of claim 25, wherein the offset distance is expressed in pixel values, and the method further comprises converting the offset distance from pixel values to length units.

27. The method of claim 21, wherein the converted ball image has a non-circular shape.

28. The method of claim 21, wherein the second algorithm involves converting the cone image to a converted cone image that looks different from the cone image.

29. A computer product having a non-transitory medium storing a set of instructions, an execution of which will cause an imaging method to be performed, the method comprising:
  obtaining an image that includes a ball image and a cone image;
  executing a first algorithm by a processor to determine a ball center;
  executing a second algorithm by the processor to determine a cone center;
  determining an eccentricity between the determined ball center and the determined cone center; and
  using the determined ball center and one or more other parameters to determine an isocenter sag, an isocenter skew, quality data representing measurement quality, a panel shift, or any combination of the foregoing;
  wherein the first algorithm involves converting the ball image to a converted ball image that looks different from the ball image.

* * * * *